US00PP36567P2

(12) United States Plant Patent
de Mulder et al.

(10) Patent No.: US PP36,567 P2
(45) Date of Patent: Mar. 25, 2025

(54) ***FUCHSIA* PLANT NAMED 'Dofuchbalpir'**

(50) Latin Name: ***Fuchsia* X *hybrida***
Varietal Denomination: Dofuchbalpir

(71) Applicant: DUMMEN GROUP B.V., De Lier (NL)

(72) Inventors: Lieke de Mulder, Rijkevoort (NL); Arjan Koot, Oeffelt (NL)

(73) Assignee: Dümmen Group B.V., De Lier (NL)

( * ) Notice: Subject to any disclaimer, the term of this patent is extended or adjusted under 35 U.S.C. 154(b) by 78 days.

(21) Appl. No.: 18/581,379

(22) Filed: Feb. 20, 2024

(51) Int. Cl.
*A01H 6/00* (2018.01)
*A01H 5/00* (2018.01)

(52) U.S. Cl.
USPC ..... Plt./300

(58) Field of Classification Search
USPC ..... Plt./263.1, 300
See application file for complete search history.

(56) References Cited

U.S. PATENT DOCUMENTS

PP32,933 P2 * 3/2021 Valin ..... A01H 5/02
Plt./300

* cited by examiner

*Primary Examiner* — Karen M Redden
(74) *Attorney, Agent, or Firm* — C. Anne Whealy

(57) ABSTRACT

A new and distinct cultivar of *Fuchsia* plant named 'Dofuchbalpir', characterized by its relatively compact, upright and mounding plant habit; moderately vigorous growth habit and moderate growth rate; freely branching habit, dense and bushy plant form; freely flowering habit; and single-type flowers that are dark purple and purplish red in color.

1 Drawing Sheet

Botanical designation: *Fuchsia* X *hybrida*.
Cultivar denomination: 'DOFUCHBALPIR'.

STATEMENT REGARDING PRIOR DISCLOSURES BY INVENTORS AND APPLICANT/ASSIGNEE

An European Community Plant Breeder's Rights application for the instant plant was filed by the Applicant/Assignee, Dümmen Group B.V. of De Lier, The Netherlands on Sep. 28, 2023, application number 2023/2021. Foreign priority is not claimed to this application.

The Inventors and Applicant/Assignee assert that no sales, offers for sale or public distribution of the instant plant occurred more than one year prior to the effective filing date of this application.

Any information about the claimed plant would have been obtained from a direct or indirect disclosure from the Inventors and/or Applicant/Assignee. Inventors and Applicant/Assignee claim a prior art exception under 35 U.S.C. 102(b)(1) for disclosures and/or sales prior to the filing date but less than one year prior to the effective filing date.

BACKGROUND OF THE INVENTION

The present invention relates to a new and distinct cultivar of *Fuchsia* plant botanically known as *Fuchsia* X *hybrida* and hereinafter referred to by the name 'Dofuchbalpir'.

The new *Fuchsia* plant is a product of a planned breeding program conducted by the Inventors in Rheinberg, Germany. The objective of the breeding program is to create new compact and mounding *Fuchsia* plants with freely branching habit and numerous attractive flowers.

The new *Fuchsia* plant originated from a cross-pollination made by the Inventors in May, 2020 in Rheinberg, Germany of a proprietary selection of *Fuchsia* X *hybrida* identified as code number FS-0009, not patented, as the female, or seed, parent with a proprietary selection of *Fuchsia* X *hybrida* identified as code number FS-0251, not patented, as the male, or pollen, parent. The new *Fuchsia* plant was discovered and selected by the Inventors as a single flowering plant within the progeny of the stated cross-pollination in a controlled greenhouse environment in Rheinberg, Germany in February, 2021.

Asexual reproduction of the new *Fuchsia* plant by terminal vegetative cuttings in a controlled environment in Rheinberg, Germany since February, 2021 has shown that the unique features of this new *Fuchsia* plant are stable and reproduced true to type in successive generations.

SUMMARY OF THE INVENTION

Plants of the new *Fuchsia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Dofuchbalpir'. These characteristics in combination distinguish 'Dofuchbalpir' as a new and distinct *Fuchsia* plant:

1. Relatively compact, upright and mounding plant habit.
2. Moderately vigorous growth habit and moderate growth rate.
3. Freely branching habit, dense and bushy plant form.
4. Freely flowering habit.
5. Single-type flowers that are dark purple and purplish red in color.

The new *Fuchsia* plant can be compared to plants of the female parent selection. Plants of the new *Fuchsia* differ primarily from plants of the female parent selection in the following characteristics:

1. Plants of the new *Fuchsia* are more upright than and not as trailing as plants of the female parent selection.
2. Plants of the new *Fuchsia* are more freely branching than plants of the female parent selection.
3. Plants of the new *Fuchsia* and the female parent selection differ in flower color as plants of the new *Fuchsia* have dark purple and purplish red-colored flowers whereas plants of the female parent selection have purple and red-colored flowers.

The new *Fuchsia* plant can be compared to plants of the male parent selection. Plants of the new *Fuchsia* differ primarily from plants of the male parent selection in the following characteristics:

1. Plants of the new *Fuchsia* are more compact than and not as vigorous as plants of the male parent selection.
2. Plants of the new *Fuchsia* are more upright than and not as outwardly spreading as plants of the male parent selection.
3. Plants of the new *Fuchsia* are more freely branching than plants of the male parent selection.

Plants of the new *Fuchsia* can be compared to plants of *Fuchsia* X *hybrida* 'Bella *Fuchsia*® Vera', not patented. In side-by-side comparisons, plants of the new *Fuchsia* and 'Bella *Fuchsia*® Vera' differ in the following characteristics:

1. Plants of the new *Fuchsia* are more upright than and not as trailing as plants of 'Bella *Fuchsia*® Vera'.
2. Plants of the new *Fuchsia* are more freely branching than plants of 'Bella *Fuchsia*® Vera'.
3. Plants of the new *Fuchsia* have smaller leaves than plants of 'Bella *Fuchsia*® Vera'.
4. Plants of the new *Fuchsia* are more freely flowering than plants of 'Bella *Fuchsia*® Vera'.

BRIEF DESCRIPTION OF THE PHOTOGRAPH

The accompanying colored photograph illustrates the overall appearance of the new *Fuchsia* plant showing the colors as true as it is reasonably possible to obtain in colored reproductions of this type. Colors in the photograph may differ slightly from the color values cited in the detailed botanical description which accurately describe the colors of the new *Fuchsia*.

The photograph is a side perspective view of a typical flowering plant of 'Dofuchbalpir' grown in a container.

DETAILED BOTANICAL DESCRIPTION

The aforementioned photograph and following observations, measurements and values describe plants grown during the spring and early summer in 22-cm containers in a glass-covered greenhouse in Rheinberg, Germany and under cultural practices and environmental conditions typically used in commercial *Fuchsia* production. During the production of the plants, day and night temperatures averaged 18° C. and light levels averaged 4,500 lux. Plants were twelve weeks old when the photograph was taken and 25 weeks old when the description was taken. In the following description, color references are made to The Royal Horticultural Society Colour Chart, Fifth Edition, except where general terms of ordinary dictionary significance are used.

Botanical classification: *Fuchsia* X *hybrida* 'Dofuchbalpir'.

Parentage:

*Female, or seed, parent*.—Proprietary selection of *Fuchsia* X *hybrida* identified as code number FS-0009, not patented.

*Male, or pollen, parent*.—Proprietary selection of *Fuchsia* X *hybrida* identified as code number FS-0251, not patented.

Propagation:

*Type*.—By vegetative terminal cuttings.

*Time to initiate roots, summer*.—About five days at temperatures about 20° C.

*Time to initiate roots, winter*.—About seven days at temperatures about 20° C.

*Time to produce a rooted plant, summer*.—About three weeks at temperatures about 20° C.

*Time to produce a rooted plant, winter*.—About four weeks at temperatures about 20° C.

*Root description*.—Fine, fibrous; typically white in color, actual color of the roots is dependent on substrate composition, water quality, fertilizers, substrate temperature and age of roots; tuber development has not been observed on plants of the new Dahlia.

*Rooting habit*.—Moderately freely branching; medium density.

*Rooting habit*.—Freely branching; dense.

Plant description:

*Plant and growth habit*.—Relatively compact, upright and mounding growth habit; freely branching habit with about three primary lateral branches each with about eleven secondary lateral branches developing per plant; pinching enhances lateral branch development; dense and bushy plant form; moderately vigorous growth habit and moderate growth rate.

*Plant height, soil level to top of foliar plane*.—About 27 cm.

*Plant height, soil level to top of floral plane*.—About 29 cm.

*Plant diameter*.—About 30.5 cm.

Lateral branch description:

*Length*.—About 26.5 cm.

*Diameter*.—About 4 mm.

*Internode length*.—About 2.3 cm.

*Strength*.—Moderately strong.

*Aspect*.—Mostly upright to somewhat outwardly.

*Texture and luster*.—Pubescent; semi-glossy.

*Color, developing*.—Close to 138A.

*Color, developed*.—Close to N186C.

Leaf description:

*Arrangement*.—Decussate, simple.

*Length*.—About 3.5 cm.

*Width*.—About 1.4 cm.

*Shape*.—Ovate, elongate.

*Apex*.—Apiculate.

*Base*.—Obtuse.

*Margin*.—Serrate to dentate.

*Texture and luster, upper and lower surfaces*.—Slightly pubescent; velvety; semi-glossy.

*Venation pattern*.—Pinnate; arcuate.

*Color*.—Developing leaves, upper surface: Close to 137B. Developing leaves, lower surface: Close to 138A to 138B. Fully expanded leaves, upper surface: Close to 137A to 137B; venation, close to 147C.

Fully expanded leaves, lower surface: Close to 146B; venation, close to 148A to 148B.

*Petioles*.—Length: About 1.3 cm. Diameter: About 1.6 mm. Texture and luster, upper and lower surfaces: Smooth, glabrous; semi-glossy. Strength: Moderately strong. Color, upper and lower surfaces: Close to 146B and 187C to 187D.

Flower description:

*Flower arrangement and habit*.—Single axillary flowers; flowers single-types and radially symmetrical; flowers initially upright and then pendulous; freely flowering habit, typically one to two flowers develop per leaf axil; at one time, about 104 developing and open flowers per plant.

*Fragrance*.—None detected.

*Time to flower and natural flowering season*.—Early flowering habit, plants begin flowering about ten weeks after planting; in the garden in The Netherlands, plants flower continuously throughout the spring and early summer.

*Flower longevity*.—Depending on temperature, flowers last about three to six days on the plant; flowers persistent.

*Flower buds*.—Length: About 2.3 cm. Diameter: About 8.7 mm. Shape: Spherical to ovoid. Texture and luster: Smooth, glabrous; semi-glossy. Color: Close to 53C.

*Flower diameter*.—About 1.35 cm by 1.5 cm.

*Flower height* (*depth*).—About 3.2 cm.

*Petals*.—Quantity of petals and arrangement: Typically four petals arranged in a single whorl; petals imbricate. Length: About 1.5 cm. Width: About 1.6 cm. Shape: Obcordate. Apex: Emarginate to rounded. Base: Attenuate. Margin: Entire; not undulate. Texture and luster, upper and lower surfaces: Smooth, glabrous; matte. Color: When opening, upper surface: Close to 79C and towards the base, close to 54C. When opening, lower surface: Close to 79B and towards the base, close to 54C. Fully opened, upper and lower surfaces: Close to 79B and towards the base, close to 54C; venation, close to 53C; color does not change with subsequent development.

*Sepals*.—Quantity and arrangement: Typically four sepals arranged in a single whorl and fused at the base; calyx star-shaped. Length: About 2.3 cm. Width: About 1 cm. Shape: Elliptic. Apex: Acute. Margin: Entire. Texture and luster, upper surface: Rough, glabrous; matte. Texture and luster, lower surface: Smooth, glabrous; semi- glossy. Color: When opening and fully opened, upper surface: Close to 58C; color does not change with subsequent development. When opening and fully opened, lower surface: Close to 53C; color does not change with subsequent development.

*Peduncles*.—Length: About 2.2 cm. Diameter: About 1 mm. Aspect: About 45 degrees from lateral branch axis. Strength: Moderately strong to strong. Texture and luster: Smooth, glabrous; semi-glossy. Color: Close to 146B.

*Reproductive organs*.—Stamens: Quantity: About eight per flower. Filament length: About 2 cm. Filament color: Close to N66B. Anther size: About 2.7 mm. Anther shape: Ellipsoidal. Anther color: Close to 161C and 63A to 63D. Pollen amount: Scarce. Pollen color: Close to 158A. Pistils: Quantity: One per flower. Pistil length: About 6.4 cm. Style length: About 5.2 cm. Style color: Close to 63B, 63C, 63D and 157D. Stigma diameter: About 1.3 mm. Stigma shape: Oval. Stigma color: Close to 59A. Ovary color: Close to 143A.

*Fruits*.—Length: About 8 mm. Diameter: About 4 mm. Texture: Rough. Color: Close to 146A.

*Seeds*.—To date, seed development has not been observed on plants of the new *Fuchsia*.

Pathogen & pest resistance: To date, plants of the new *Fuchsia* have not been observed to be resistant to pests and pathogens common to *Fuchsia* plants.

Temperature tolerance: Plants of the new *Fuchsia* have been observed to tolerate temperatures ranging from about 5° C. to about 40° C.

It is claimed:

1. A new and distinct *Fuchsia* plant named 'Dofuchbalpir' as illustrated and described.

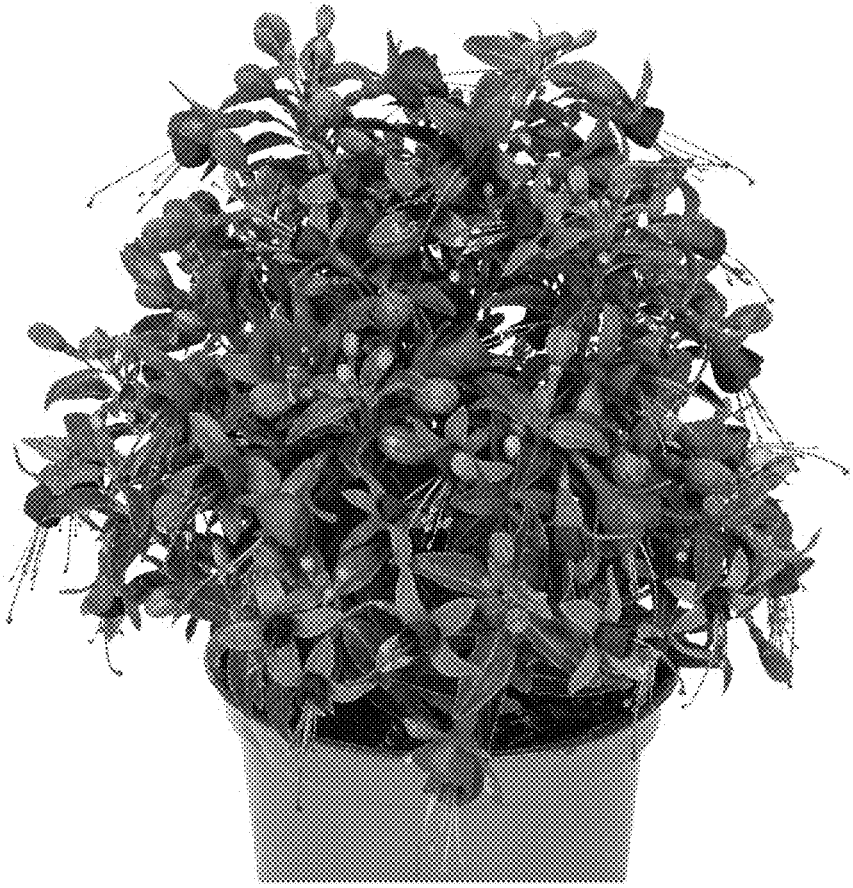

* * * * *